United States Patent
Dicarlo et al.

(10) Patent No.: US 8,211,088 B2
(45) Date of Patent: Jul. 3, 2012

(54) CATHETER WITH CONTROLLED LUMEN RECOVERY

(75) Inventors: Paul Dicarlo, Middleboro, MA (US); Kristine H. Atkinson, Winchester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1216 days.

(21) Appl. No.: 11/251,475

(22) Filed: Oct. 14, 2005

(65) Prior Publication Data

US 2007/0088322 A1 Apr. 19, 2007

(51) Int. Cl.
*A61M 25/00* (2006.01)
(52) U.S. Cl. .................. 604/523; 604/524
(58) Field of Classification Search .................. 604/246, 604/523, 524
See application file for complete search history.

(56) References Cited

U.S. PATENT DOCUMENTS

| | | | |
|---|---|---|---|
| 3,901,965 A | 8/1975 | Honeyman, III | |
| 4,660,560 A | 4/1987 | Klein | |
| 5,954,744 A | 9/1999 | Phan et al. | |
| 6,514,237 B1 * | 2/2003 | Maseda | 604/533 |
| 6,517,539 B1 | 2/2003 | Smith et al. | |
| 6,547,724 B1 | 4/2003 | Soble et al. | |
| 6,648,863 B2 | 11/2003 | Reever | |
| 6,656,146 B1 | 12/2003 | Clayman et al. | |
| 6,776,945 B2 | 8/2004 | Chin et al. | |
| 7,338,509 B2 * | 3/2008 | Mattison | 606/192 |
| 2004/0019358 A1 | 1/2004 | Kear | |
| 2004/0068161 A1 | 4/2004 | Couvillon, Jr. | |
| 2004/0111009 A1 | 6/2004 | Adams et al. | |
| 2005/0027198 A1 | 2/2005 | Couvillon, Jr. | |
| 2005/0027244 A1 * | 2/2005 | Eidenschink | 604/95.05 |
| 2005/0080459 A1 * | 4/2005 | Jacobson et al. | 607/9 |
| 2005/0102017 A1 * | 5/2005 | Mattison | 623/1.11 |
| 2005/0165439 A1 * | 7/2005 | Weber et al. | 606/191 |
| 2005/0256549 A1 * | 11/2005 | Holzer | 607/35 |
| 2005/0261563 A1 * | 11/2005 | Zhou et al. | 600/347 |
| 2006/0111618 A1 * | 5/2006 | Couvillon, Jr. | 600/152 |
| 2007/0038224 A1 * | 2/2007 | Ortiz | 606/108 |

FOREIGN PATENT DOCUMENTS

| | | |
|---|---|---|
| EP | 1 077 049 | 2/2001 |
| EP | 1526887 A2 | 5/2005 |

* cited by examiner

*Primary Examiner* — Nicholas Lucchesi
*Assistant Examiner* — Gerald Landry, II
(74) *Attorney, Agent, or Firm* — Fay Kaplun & Marcin, LLP

(57) ABSTRACT

An implantable medical device, comprising a body including a lumen extending therethrough at least one activatable element disposed within the body, a dimension of each of the at least one activatable elements changing in response to a predetermined stimulation between an activated state and an inactivate state to change a shape of the body to control a degree of opening of the lumen and at least one actuation element, each of the at least one actuation elements being configured to selectively supply the predetermined stimulation to a corresponding one of the at least one activatable elements to move the corresponding one of the at least one activatable elements between the activated and inactive states.

27 Claims, 2 Drawing Sheets

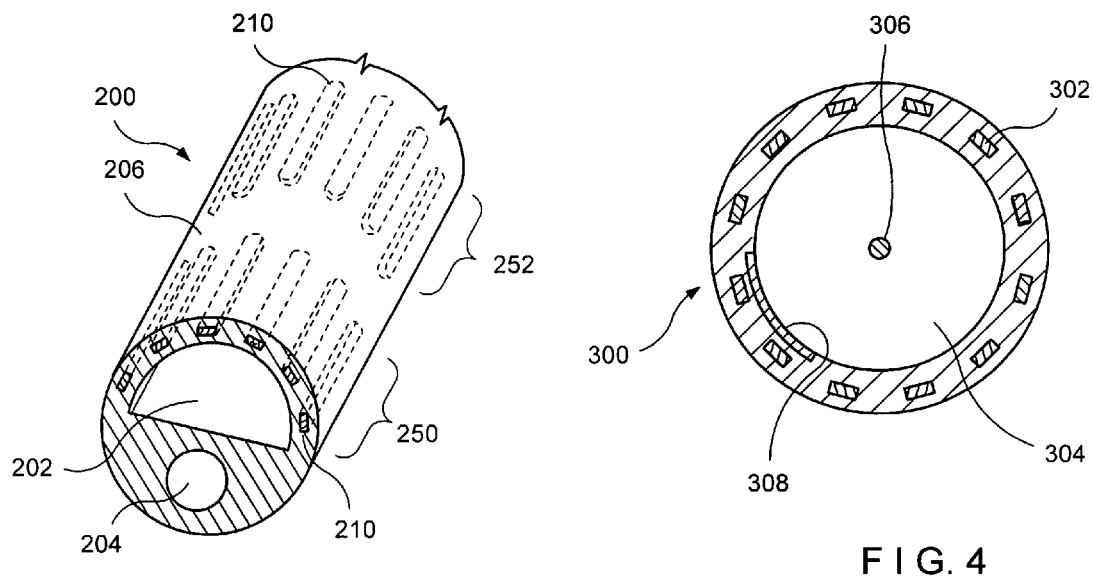
FIG. 3
FIG. 4
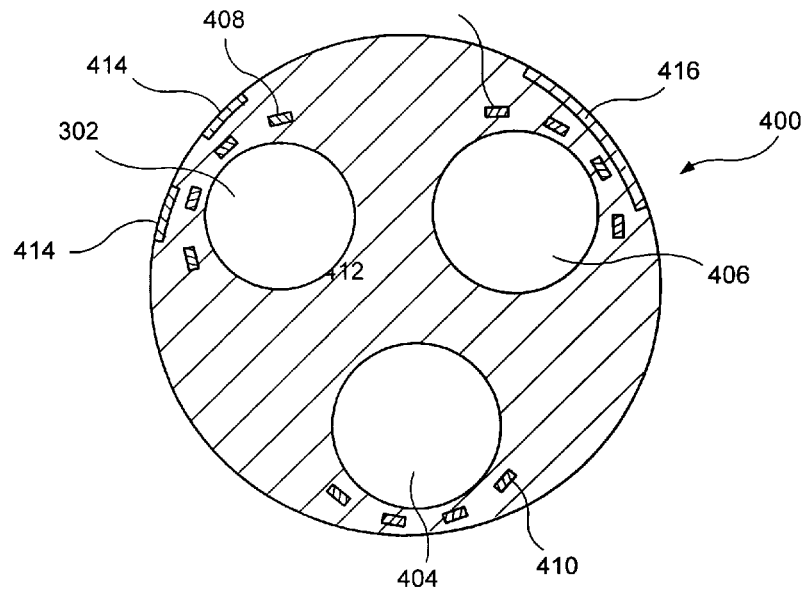
FIG. 5

US 8,211,088 B2

CATHETER WITH CONTROLLED LUMEN RECOVERY

BACKGROUND OF THE INVENTION

Catheters are commonly used for a wide variety of purposes including draining fluids from and introducing fluids to the body. In certain cases, a catheter may be semi-permanently placed to form a path to and from the body for repeated fluid transfers.

Several problems commonly associated with placing foreign elements such as catheters within the body for extended periods are not easily solved. In the case of a permanently or semi-permanently placed catheter, for example, biological materials may form occlusions or partial blockages within the catheter lumen. For example, blockages may be formed by precipitates from fluids flowing through the catheter or, for catheters through which blood is to flow, a blood clot or fibrin buildup may accumulate in the lumen.

In addition, the flow through a catheter may be reduced or completely blocked by mechanical constriction of the lumen. For example, kinks may form in the catheter as the patient moves about or because of imperfect placement of the catheter. If the catheter is bent along a radius of curvature smaller than a critical radius, the catheter's lumen may collapse significantly reducing its cross-sectional area. Clearing an occlusion or removing a mechanical constriction of a lumen of an implanted catheter may entail removing the catheter and replacing it.

To prevent lumen collapse during insertion, conventional catheters are often constructed of materials which have inherently good column strength. However, the catheters formed by these materials may lack other desirable qualities. For example, softer catheters which permit increased patient mobility may be avoided in favor of stiffer catheters (i.e., catheters with higher column strengths) which more effectively resist lumen collapse.

SUMMARY OF THE INVENTION

The present invention is directed to an implantable medical device, comprising a body including a lumen extending therethrough and at least one active element formed of electroactive polymer disposed within the body, a dimension of each of the at least one active elements changing in response to a predetermined electrical stimulation between an activated state and an inactive state to change a shape of the body to control a degree of opening of the lumen in combination with at least one electrical actuation element, each of the at least one electrical actuation elements being configured to selectively supply a stimulation current to a corresponding one of the at least one activatable elements to move the corresponding one of the at least one activatable elements between the activated and inactive states.

BRIEF DESCRIPTION OF THE DRAWINGS

FIG. 3 is a perspective view showing an embodiment of a catheter according to the present invention with a segmented activatable material;

FIG. 4 is a cross sectional view showing another embodiment of a catheter according to the invention; and FIG. 5 is a cross sectional view showing a different embodiment of a catheter according to the present invention.

DETAILED DESCRIPTION

Figure 1:
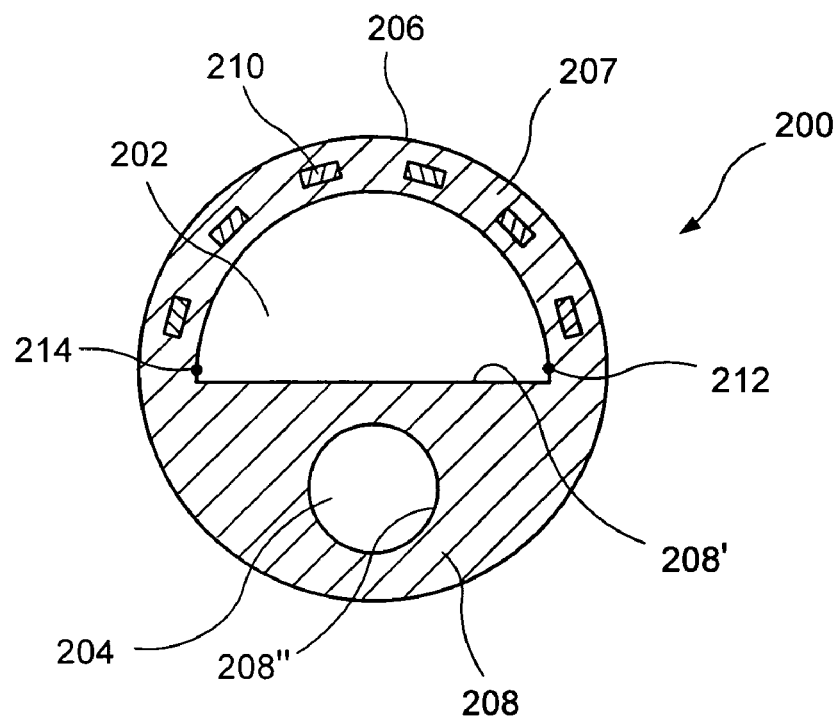
FIG. 1 is a cross sectional view showing a catheter according to an embodiment of the invention in an operative configuration.

The present invention may be further understood with reference to the following description and the appended drawings, wherein like elements are referred to with the same reference numerals. The invention is related to medical devices used to introduce fluids to and/or remove fluids from the body.

A catheter is basically a tube formed as an outer shell defining one or more inner lumens which may be used, for example, as fluid conduits. Various fittings or connections may be coupled to the ends of a catheter, for example, to connect the proximal end (i.e., the end closest to a user of the device) to additional medical devices. The outer shell is typically formed of a material impermeable to the fluid flowing therein with the length and diameter varying considerably depending on the application for which the catheter is intended. Catheters may be from a few millimeters to a meter or more in length and may have a diameter ranging from less than a millimeter to more than a centimeter. As would be understood by those skilled in the art, catheters may be made from a wide range of materials so long as they are biocompatible, and exhibit the required column strength, flexibility, etc. These catheters are most often formed of polymers including, for example, polyurethanes, carbothanes, polyesters, and other materials known in the art.

Patency (i.e., the state of unrestricted flow through a conduit) may be reduced or stopped by, for example, the build-up of biological material or mechanical constriction of one or more of the catheters lumens. For example, a lumen may collapse when a compressive load is applied which the column strength of the catheter is insufficient to withstand forces applied thereto or when the catheter must accommodate a radius smaller than a critical bending radius. Those skilled in the art will understand that the teachings of the present invention apply equally well to other tubes which may be inserted into the body and which, due to any or a combination of various of these causes may suffer from reduction in cross-sectional area of parts of lumens or channels extending therethrough. Thus, although the present invention is described in detail in regard to catheters, it is to be understood that the term catheter is to be interpreted broadly to include any tube insertable into the body to, for example, deliver minimally invasive tools, agents, sensors, treatments, etc.

Those skilled in the art will understand that this invention is particularly suited for tubular members which remain within the body for extended periods of time and which, during this time may become blocked or kinked. For example, the lumens of semi-permanently implanted single and multi-lumen catheters such as peripherally inserted central catheters, venous catheters and dialysis catheters may need to be reopened after prolonged use. In addition, as described below ureteral stents and urethral drains may benefit from the teachings of the invention with arrangements substantially similar to those described in regard to single lumen catheters.

According to the embodiments of the present invention, a catheter is provided which can restore fluid flow through the lumen(s) in the case of either lumen collapse or the formation of a blockage within the lumen. The favorable properties of the catheters according to the invention derive in part from the use of activatable materials, which can change shape in response to external stimuli. By providing those stimuli at selected times, locations and intensities, it is possible to change the shape and properties of the materials and of the catheter formed therefrom. Those skilled in the art will understand that, although the embodiments of the invention described in detail herein focus on the use of electroactive polymers and electrical stimulation, any activatable material, polymer or otherwise, which changes shape in response to a predetermined stimulus may be substituted for the activatable materials described herein. For example, otherwise suitable materials which change shape in response to any form of electromagnetic energy or chemical stimulus, etc. may be employed in a catheter according to the present invention.

Electroactive polymers (EAP) are a class of materials which expand or contract depending on a voltage applied thereto. As would be understood by those skilled in the art, by controlling an amount, placement and pattern of EAP within a structure and applying energy thereto, the shape of the structure may be changed. EAP materials have been used as micro-actuators to carry out changes in the configuration of small devices.

EAP materials are generally sorted into two classes based on their activation mechanisms: 1) electronic EAP activated by coulomb forces (e.g., including electrostrictive, electrostatic, piezoelectric and ferroelectric forces); and 2) ionic EAP materials operating under the principles of mobility or diffusion of ions.

Electronic EAP materials can be made to hold an induced displacement during activation by a DC voltage. This property makes electronic EAP materials useful for robotic applications, where they can be used as motion actuators. Electronic EAP materials have a large mechanical energy density, meaning that they can apply a relatively large mechanical force for their size. Some of the electronic EAP materials commonly used include dielectric EAP, electrostrictive graft elastomers, electrostrictive paper, electro-viscoelastic paper, ferroelectric polymers and liquid crystal elastomers. The entire disclosure of US Patent Application Publication No. 20040068161 to Couvillon which describes various EAP materials and EAP actuators is hereby expressly incorporated by reference herein.

Some of the more commonly used ionic EAP comprise carbon nanotubes, conductive polymers, electrorheological fluids, ionic polymer gels, and ionic polymer metallic composites. In general, ionic EAP operate at a lower voltage than electronic EAP and provide a predominantly bending actuation exhibiting large displacements. However, the response times for ionic EAP are greater than those of electronic EAP and these materials are often unable to maintain a strain under a DC voltage, apply lower bending actuation forces and must be maintained in an aqueous system (for example, to sustain hydrolysis at >1.23V). In addition, except for CP and Carbon Nanotubes, it has proven difficult to produce these materials in a consistent manner.

As mentioned above, the induced displacement obtained from both ionic and electronic EAP may be harnessed to modify the shape of components made therefrom. As would be understood by those skilled in the art, activatable components made from, for example, EAP, magnetically or light activated polymers and/or thermally activated gels may be designed geometrically to bend, stretch or contract under certain conditions.

According to an exemplary embodiment of the invention described in detail in the following paragraphs, an activating stimulus is applied to activatable components of a catheter. Different manners of actuating the activatable components may be used. For example, the EAP may be actuated by immersion in a specific chemical bath, by the use of magnetically activated polymers, thermally activated gels, and light activated polymers. These materials may be used in a manner substantially similar to the exemplary EAP discussed herein. For example, instead of an electric voltage or current being applied to the materials to actuate them, the stimulus may be a magnetic field, a light, or a chemical solution applied to the material to cause bending, elongation or contraction. Useful regions of the electromagnetic spectrum for stimulation are radio, microwave, infrared, visible light and ultraviolet wavelengths. Those skilled in the art will understand that shape memory alloys and/or inflatable structures may also be used to alter the shape of a medical element such as a catheter, without major modifications being made to the exemplary embodiments.

According to exemplary embodiments of the present invention, a collapsed or occluded lumen of a catheter may be propped open by using an activatable material designed to respond to a stimulus. For example, EAP may be used to modify the lumen walls of a catheter to recover a desired shape of the wall to reopen a constricted or occluded lumen. FIG. 1 shows an exemplary embodiment of a catheter 200 according to the invention, having a circular lumen 204 and a larger lumen 202 shaped as part of a circle (e.g., lunette, "D" shaped, semi-circular, etc.) extending longitudinally along the catheter's length.

As shown in FIG. 1, the catheter 200 is operating normally with both lumens 202, 204 fully patent to flow. The lumen 202 of the catheter 200 is defined by a luminal surface of a first portion 207 of a wall 206 of the catheter and a first luminal surface 208' of a second portion 208 of the wall 206. The first portion 207 defines a substantially convex portion of the lumen 202 and constitutes a portion of the wall 206 at which a cross-sectional thickness thereof is a minimum. Because it is the thinnest portion of the wall 206, the first portion 207 is most likely to collapse or kink when the catheter 200 is subject to an excessive load or negative pressure or is bent around a tight radius. A plurality of activatable material elements 210 are disposed in the first portion 207 of the wall 206 of this exemplary embodiment and may include, for example, fibers formed of an EAP. In the condition shown in FIG. 1, the activatable material elements 210 do not need to be activated to change the shape of the catheter 200 as the lumens 202, 204 are fully open and the catheter 200 is operating normally. However, depending on the stresses applied to the catheter 200, the activatable material elements 210 may need to be activated to maintain the current shape of the catheter 200.

Figure 2:
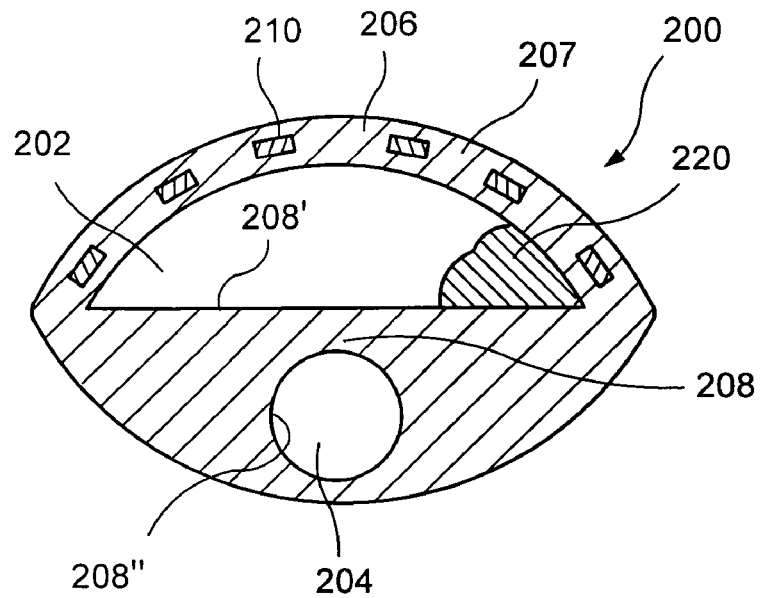
FIG. 2 is a cross sectional view showing the catheter shown in FIG. 1 in a collapsed configuration.

FIG. 2 shows a cross section of the same exemplary catheter 200 in a condition where the first portion 207 of the wall 206 has collapsed or has been pinched. In this condition, the cross sectional area of the lumen 202 has been considerably reduced, and in extreme cases may be reduced substantially to zero. As described above, the condition shown in FIG. 2 may result from the first portion 207 of the wall 206 buckling and collapsing the luminal surface against itself. The collapse may, for example, be the result of exceeding the column strength of the outer wall 206 of catheter 200 during insertion or when a kink is formed, for example, when the catheter 200 is bent around a radius of curvature smaller than its critical radius of curvature. The critical radius of curvature indicates a minimum radius about which the catheter 200 may be bent without at least one of the lumens 202, 204 deforming or collapsing.

The lumen 202 of FIG. 2 also shows an occlusion 220 partially blocking flow through the catheter 200. In more severe cases this blockage may be complete. As would be understood by those skilled in the art, the occlusion 220 may be formed as precipitates from the fluid flowing through the catheter 200 accumulate at a location within the lumen 202 (e.g., an area where the flow rate is relatively low). In other cases, an occlusion 220 may result from thrombosis, where a blood clot or a buildup of fibrin attaches to a wall of the lumen 202. These blockages may exist together with or independent of the mechanical impediments to the flow descried above. In the view of FIG. 2, the activatable material elements 210 are not yet in an actuated configuration and follow the general contour of the collapsed wall 206.

As described above, an array of expansive EAP elements is incorporated on or embedded near a luminal surface of the wall 206 surrounding the lumen 202. That is, although FIG. 2 shows the EAP elements embedded within the first portion 207 of the wall 206, EAP elements may be included throughout or in various parts of one or both of the first portion 207 and the second portion 208 of the wall 206. The EAP elements are preferably arrayed in such a manner that, contraction and/or expansion of the EAP elements cause a change in the shape and configuration of at least one of the first portion 207 and the second portion 208. Furthermore, the changes in shape may be substantially limited to the luminal surfaces of the first and second portions 207, 208, respectively, or may alter the shape of an outer surface of the wall 206. For example, the array of EAP elements preferably comprises a plurality of elements 210 arrayed along one surface of the internal lumen 202, or which may be more generally incorporated in a matrix of the wall 206. The activatable elements 210 are preferably selected for their ability to react to a stimulus, for example an electric current, by expanding or by contracting when the stimulus is applied. Those skilled in the art will understand that, in order to influence the state of a lumen, it is most effective to incorporate the elements 210 on the surface of a wall of the lumen or embedded as near as possible to a surface of the wall of the lumen. For example, EAP fibers may be spun over the surface of the lumen (surfacial, spanning, fuzzy) or as a liner, sprayed, printed, flocked or cast thereon.

According to the exemplary embodiment of the invention, the EAP used in the catheter 200 is an expansive EAP, such as polyacrylonitrile-nanofibers (PAN-N). After a mechanical collapse of the catheter 200 as shown in FIG. 2, the EAP elements 210 arrayed within the first portion 207 of the wall 206 are stimulated in the region of the collapse to expand the elements 210 to restore the shape of the lumen and to force the stricture open and restore flow through the lumen 202. Those skilled in the art will understand that, to more effectively open the lumen 202, the EAP elements 210 are preferably incorporated contiguous to or very near a surface of the lumen 202. The configuration of the EAP elements 210 within the wall 206 may be selected so that, for example, an outer surface of the wall 206 extends longitudinally and/or expands radially outward when the EAP material 210 is stimulated. The orientation and placement of the EAP material fibers is preferably such that the collapse of the lumen 202 is countered most effectively. For example, if the EAP elements 210 are substantially linear and are arranged substantially parallel to a longitudinal axis of the catheter 200, expansion of the EAP elements 210 will stretch the catheter 200 longitudinally. However, if the EAP elements 210 extend around this axis, for example, along coils, expansion of these EAP elements 210 will radially expand the catheter 200 and the lumen 202. If the catheter 200 is formed of a compressible material, the wall of the catheter 200 will thin as the lumen 202 expands creating a louvered profile that may aid in delivery of the catheter 200.

The exemplary embodiment of the invention described herein may also be used to clear a protein or material occlusion formed in the lumen 202, for example similar to the occlusion 220 shown in FIG. 2. The occlusion may be removed, for example, by electromechanically "burping" the catheter 200 in the region surrounding the occlusion in a peristaltic manner. The EAP elements 210 in that region may be alternatively expanded and contracted, by cyclically applying the excitation field to selected individuals in the array of elements 210. The cyclical burping flexes the first portion of the wall 206 to break the mooring of the occlusion allowing the occlusion to be suctioned off, filtered or flushed out, depending on the location and accessibility of the catheter 200. The flexing of first portion 207 the catheter wall 206 may be caused by stimulating individual EAP elements 210 along the circumference of the catheter 200, for example from a starting point 212 to an end point 214.

Alternatively, the EAP elements 210 may have separate segments in the longitudinal direction, as shown in FIG. 3. In that case, the EAP elements 210 in region 250 may be activated separately from the elements 210 in region 252, to obtain a longitudinal flexing of the first portion 207 of the wall 206. In a different embodiment, the elements 210 may be activated along only certain longitudinal segments, also resulting in a longitudinal flexing of the wall 206. This arrangement may be suitable for straightening a kinked segment, for example, near an attachment of the catheter to an implanted port. If the EAP elements 210 extend around the axis of the catheter 200, activating and deactivating longitudinally separate segments of the EAP elements 210 will expand and contract these segments allowing the catheter 200 to be burped in sections to, for example, clear obstructions.

In the exemplary embodiments described above, the EAP elements 210 are shown only in the first portion 207 of the wall 206. However, in different embodiments, EAP elements 210 may completely surround the affected lumen. For example, as shown in FIG. 4, EAP fibers 302 are disposed substantially symmetrically around a lumen 304 of a catheter 300. The actual disposition of the activatable material may be selected depending on the geometry of the affected catheters and of the lumens. The expected pattern of loads to be experienced by the catheter may also be considered in defining the extent and arrangement of the array of EAP fibers. Generally, the EAP may be incorporated in or on regions of the catheter which are more likely to collapse during use. Typically, the thinner walls surrounding lumens will be more likely to collapse and EAP structures of varying types and compositions may be concentrated in these areas. Alternatively, the EAP elements may be activated by one or more transformers implanted within the body to generate an electric field near the activatable material. In this example, a guidewire 306 (FIG. 4) with a coil may be provided at a set location relative to the catheter with a corresponding coil 308 within the catheter. When the coil in the guidewire 306 is activated by a current, the coil 308 in the catheter is energized by induction to stimulate the EAP elements. According to the exemplary embodiment, EAP elements along the length of the coil 308 are stimulated, thus providing a measure of control over the location where the material reacts. The shape and location of the coil(s) 308 may also be varied to achieve different results. In addition, as would be understood by those skilled in the art, creating an array of EAP structures with different responses to a single stimulus (or which are activated together by different stimuli) may result in a twisting effect. For example, contracting EAP structures in a first portion of a wall of a catheter while expanding EAP structures in a second portion of the wall of the catheter which is disposed on an opposite side of a plane including an axis of the catheter may cause the catheter to twist about the axis.

As described above, a ureteral stent may be constructed according to the present invention so that it may restore flow therethrough by the activation of EAP elements included therein. For example, U.S. Pat. No. 6,656,146, the entire disclosure of which is hereby expressly incorporated by reference herein, describes a ureteral stent with tethers which extend therefrom to an accessible location. Those skilled in the art will understand that, if a ureteral stent were formed with EAP elements arranged similarly to those shown in the catheter 300 of FIG. 4, and the tethers were formed of an electrically conductive material coupled to the EAP, application of a voltage to the tethers would allow control of the behavior of the ureteral stent in the same manner as described above for the catheter 300. Similarly, a urological drain as described in U.S. Pat. No. 6,648,863, if modified to include one or more electrically conductive tethers and to include EAP elements arranged, for example, as in the catheter 300, would also allow control of the behavior of the ureteral stent in the same manner as described above for the catheter 300. The entire disclosure of U.S. Pat. No. 6,648,863 is hereby expressly incorporated by reference herein.

As shown in FIG. 5, each of the lumens 402, 404 and 406 of a multilumen catheter 400 includes a corresponding array of EAP elements 408, 410, 412, respectively, mounted in a portion of the outer wall adjacent thereto. The arrays of EAP fibers 408, 410 and 412 are preferably separate from one another with separate actuation controls so that they can be contracted and/or extended independently of one another. For instance, when only one of the lumens 402, 404, 406 is affected by an occlusion, the fibers corresponding only to that lumen may be activated to dislodge the occlusion. In other cases, for example when the catheter 400 has collapsed, all or several of the arrays of fibers 408, 410 and 412 may be activated, to restore the structural integrity of the catheter 400. However, those skilled in the art will understand that these arrays 408, 410, 412 many be interconnected for coordinated activation as well.

In addition to restoring the flow through the lumens of a catheter, embodiments of the present invention may be used to manage the pressure of the fluid flowing within the catheter. For example, by altering the radius of a selected portion of a lumen, the local fluid pressure therein may be increased (by reducing the radius) or decreased (by increasing the radius). Separate EAP fibers coupled to separate activators, for example, similar to those shown in FIG. 5, allow control of fluid pressure in selected portions of individual lumens independently of pressure in other lumens and in other portions of the lumen. In this manner, only selected portions of one or more of the lumens may be manipulated or, if desired, multiple lumens may be manipulated at the same time to achieve the desired fluid pressure levels.

The use of EAP fibers within catheter walls and in other medical lines and tubes as described herein, confers to these artificial materials some of the properties found in natural blood vessels. For example, the endothelial cells of natural blood vessels provide dynamic responses to affect blood flow pressure, and maintain the blood vessels open. Similarly, the EAP materials described in embodiments of the present invention may be used to affect large scale changes in the shape and dimensions of catheter lumens to provide a wide degree of control over flow characteristics within the catheter and to address flow problems without physically accessing the affected area.

Prefabricated fibers or film strips of EAP may be incorporated into the material of the catheters in several ways. For example, the EAP may be co-extruded with the polymer of which the catheter is to be formed, may be previously deposited on a mandrel or may be applied subsequently to the extrusion step as a coating, layer, film, paint or brand. Alternatively, the EAP may be precipitated on a previously manufactured polymer in a desired pattern by, for example, filling a lumen of the catheter with a liquid EAP mixture and irradiating it with a laser in the desired pattern. As would be understood by those skilled in the art, EAP may be arranged within or on the catheter in different patterns to achieve a desired alteration of the shape of various portions of the catheter as dictated by the specific application for which the catheter is designed. For example, the activatable material may be formed in the shape of a spiral, a radial ring, a radial column, a grid, a stellate or any other pattern which provides the desired control over the shape of the catheter and the lumens extending therethrough.

The actuation of the EAP which is part of the catheter may be achieved in a number of ways. For example, as shown in FIG. 5 a conductive element 414 extends from a hub at the proximal end of the catheter 400 to the location of the EAP fiber. A voltage applied to the conductive element 414 is controlled to achieve the desired activation of the corresponding EAP element. As would be understood by those skilled in the art, the conductive element 414 may be formed of any electrically conductive material such as, for example metals and conductive polymers. In a different embodiment, an embedded electrical coil or antenna 416 may be used in place of the hard wired conductive element 414 to activate the EAP elements in a manner similar to telemetry. In this method the signal transmitter is not in physical contact with the receiving antenna from which signals are forwarded to the EAP elements. With this method, the EAP elements may be activated through the skin and may be localized to only the site of collapse of the catheter to limit the scope of the activation to those areas where it is needed.

As indicated, a control signal may be sent to the EAP elements from a control unit of the catheter which is preferably external to the patient. The control signals may be sent over a wire or over a wireless interface, depending on the location and purpose of the catheter with the type of signals used varying in dependence on the configuration of the catheter and the application for which it is intended. For example, the signals may command the all of the EAP elements of the catheter to contract or expand, or may be encoded to affect only certain ones of EAP elements.

The exemplary embodiments of catheters according to the present invention may be used for a variety of applications. For example, long term PICC lines, shunts and port neck catheters may be fitted with actuators made from activatable materials. Dialysis catheters also are often implanted for long periods of time and can benefit from the methods of the present invention to clear collapses and occlusions of the lumen. Furthermore certain tubular support structures with substantially continuous walls (e.g., urology stents, trachea tubes and tubes for gastrointestinal applications) may also benefit from the inclusion of activatable materials in their construction as described above. Those skilled in the art will understand that a tube constructed substantially as described above may be applied for any of these purposes with a delivery device for the tube delivering electricity thereto (e.g., via a frangible link) to increase a diameter of and deploy the tube. The delivery device may then be removed leaving the tube in place. Neonatal infusion and lung respirator catheters, likewise, may be made more effective by application of the present invention. More generally, any medical product having a lumen that has to be kept free flowing may benefit from the use of activatable materials, and in particular of EAP materials as described herein.

The present invention has been described with reference to specific embodiments, and more specifically to a catheter with EAP material actuators. However, other embodiments may be devised that are applicable to other medical devices and procedures, and to other activatable materials, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive illustrative rather than restrictive sense.

What is claimed is:

1. An implantable medical device, comprising:
a body including a lumen extending therethrough; and
at least one activatable element disposed within the body, a dimension of each of the at least one activatable elements changing in response to a predetermined stimulation between an activated state and an inactive state to change a shape of the body to control a degree of opening the lumen, wherein the at least one activatable element is disposed in a portion of the body at which a cross-sectional thickness taken perpendicular to a longitudinal axis of the body is a minimum.

2. The device according to claim 1, further comprising at least one actuation element, each of the at least one actuation elements being configured to selectively supply the predetermined stimulation to a corresponding one of the at least one activatable elements to move the corresponding one of the at least one activatable elements between the activated and inactive states.

3. The device according to claim 2, wherein the at least one activatable element is formed of EAP and wherein the predetermined stimulus comprises one or more regions of the electromagnetic spectrum.

4. The device according to claim 2, wherein the predetermined stimulus is a chemical stimulus and wherein each of the at least one actuation elements supplies the chemical stimulus to the corresponding activatable element.

5. The device according to claim 3, wherein the at least one activatable element comprises a plurality of activatable elements, the activatable elements forming an array of EAP fibers.

6. The device according to claim 3, further comprising a control unit coupled to the at least one electrical actuation element to supply stimulation current thereto.

7. The device according to claim 6, wherein the control unit is remote from the catheter.

8. The device according to claim 1, wherein the activatable elements are disposed radially outside of the lumen, and extend longitudinally along the lumen.

9. The device according to claim 3, further comprising a first inductive coil disposed coupled to the at least one electrical actuation element, the first inductive coil being located adjacent to the at least one activatable element for receiving a magnetic field induced from a second inductive coil external to the body.

10. The device according to claim 9, wherein the second inductive coil is coupled to a guidewire.

11. The device according to claim 3, wherein the electrical actuation element comprises an electrical conductor extending from the at least one actuation element to a source of electric current.

12. The device according to claim 3, further comprising an antenna disposed adjacent to the activatable elements for receiving the stimulation current from a remote control unit.

13. The device according to claim 3, wherein the EAP is one of an electronic EAP and an ionic EAP.

14. The device according to claim 13, wherein the EAP comprises at least one of dielectric EAP's, electrostrictive graft elastomers, electrostrictive paper, electro-viscoelastic paper, ferroelectric polymers, liquid crystal elastomer carbon nanotubes, conductive polymers, electrorheological fluids, ionic polymer gels, and ionic polymer metallic composites.

15. The device according to claim 1, wherein the at least one activatable element is one of coextruded with the body, coating and a precipitate.

16. A catheter comprising:
an elongated body defining a lumen;
a polymeric material forming a wall of the elongated body; and
a plurality of activatable material elements a size of which, when subjected to a predetermined stimulation, changes from an inactive state to an activated state, the activatable material elements being coupled to the wall in a pattern selected so that, when placed in the activated state, the activatable material elements draw the wall into a predetermined shape to control an opening of the lumen, wherein the activatable elements are disposed in a portion of the body at which a cross-sectional thickness taken perpendicular to a longitudinal axis of the elongated body is a minimum.

17. The catheter of claim 16, further comprising at least one actuation element stimulating the activatable material elements.

18. The catheter of claim 17, further comprising a control unit operatively connected to the actuation elements for controlling stimulation of the activatable material elements.

19. The catheter of claim 16, wherein the plurality of activatable material elements comprises an array of activatable material fibers disposed longitudinally around a circumference of the lumen.

20. The catheter of claim 17, wherein, when in the activated state, the activatable material elements radially constrict to expand the lumen.

21. The catheter of claim 18, wherein the activatable elements comprise an array of activatable material fibers and the control unit stimulates a first portion of the fibers of the array independently of a second portion thereof to expand and contract to mechanically dislodge an occlusion in the lumen.

22. The catheter of claim 18, wherein the control unit stimulates a first longitudinal segment of the activatable material elements independently of a second longitudinal segment thereof to mechanically dislodge an occlusion of the lumen.

23. The catheter of claim 18, further comprising a plurality of lumens and a corresponding plurality of arrays of activatable material elements, each of the arrays being disposed around a corresponding one of the plurality of lumens and being individually controllable to independently alter the openings of the lumen.

24. The catheter of claim 18, wherein the activatable material elements are disposed around the lumen in one of a spiral, a radial ring, a radial column, a grid and a stellate.

25. The catheter of claim 16, wherein the activatable material elements comprise at least one of an EAP, a material altering in size in reaction to a magnetic field, a material altering in size in reaction to a chemical solution, a material altering in size in reaction to light, and a shape memory alloy.

26. The catheter of claim 25, wherein the activatable material elements comprise EAP further including an electrical conductor providing to the activatable material elements a stimulating current.

27. The catheter of claim 26, further comprising an inductive coil providing the stimulating current to the electrical conductor.

* * * * *